US010400198B2

(12) United States Patent
Ferguson et al.

(10) Patent No.: US 10,400,198 B2
(45) Date of Patent: Sep. 3, 2019

(54) METHOD OF SANITIZING A SURFACE

(71) Applicants: Eagle US 2 LLC, Houston, TX (US); Southeastern Systems, Inc., Conyers, GA (US)

(72) Inventors: Richard H. Ferguson, Cecil, PA (US); Christopher M. Kareis, Pittsburgh, PA (US); Walter Neal Stanford, Conyers, GA (US); Michael Eugene Allen, Conyers, GA (US)

(73) Assignees: EAGLE US 2 LLC, Houston, TX (US); SOUTHEASTERN SYSTEMS, INC., Conyers, GA (US)

( * ) Notice: Subject to any disclaimer, the term of this patent is extended or adjusted under 35 U.S.C. 154(b) by 58 days.

(21) Appl. No.: 15/679,213

(22) Filed: Aug. 17, 2017

(65) Prior Publication Data
US 2018/0057774 A1    Mar. 1, 2018

Related U.S. Application Data

(60) Provisional application No. 62/379,305, filed on Aug. 25, 2016.

(51) Int. Cl.
*C11D 7/28*   (2006.01)
*A22C 21/00*  (2006.01)
(Continued)

(52) U.S. Cl.
CPC ............... *C11D 7/28* (2013.01); *A01N 59/00* (2013.01); *A22B 5/0082* (2013.01);
(Continued)

(58) Field of Classification Search
CPC .. A01N 59/00; A22B 5/0082; A22C 21/0061; A23B 4/20; A23B 4/24; A23B 4/30;
(Continued)

(56) References Cited

U.S. PATENT DOCUMENTS 3,276,949 A   10/1966   Robson et al.
3,856,932 A   12/1974   May
(Continued)

FOREIGN PATENT DOCUMENTS

CN   101073319 A   11/2007
WO     03055797 A1    7/2003
(Continued)

OTHER PUBLICATIONS

Evaluation of Water Acidification Products, Nov. 2008, http://www.thepoultrysite.com/articles/1214/evaluation-of-water-acidification-products.

*Primary Examiner* — Timothy C Cleveland
(74) *Attorney, Agent, or Firm* — The Webb Law Firm

(57) ABSTRACT

A method of sanitizing a surface is described that includes: (a) providing a pH control composition that includes at least one pH control agent (such as sodium bisulfate); (b) contacting a first feed aqueous stream with the pH control composition, thereby forming a first treated aqueous stream; (c) combining at least a portion of the first treated aqueous stream with a feed sanitizing aqueous stream that includes free available halogen, thereby forming a treated sanitizing aqueous stream that includes free available halogen (such as free available chlorine). The surface sanitizing method further includes, (d) elevating the temperature of the treated sanitizing aqueous stream, thereby forming a heated treated sanitizing aqueous stream having an elevated temperature that includes free available halogen. The heated treated sanitizing aqueous stream is applied to a surface to be sanitized (such as a poultry carcass surface).

18 Claims, 3 Drawing Sheets

(51) Int. Cl.

| | | |
|---|---|---|
| *C11D 3/48* | (2006.01) | |
| *C11D 17/00* | (2006.01) | |
| *A23L 3/3508* | (2006.01) | |
| *A23L 3/3526* | (2006.01) | |
| *A23L 3/358* | (2006.01) | |
| *A22B 5/00* | (2006.01) | |
| *A23B 4/20* | (2006.01) | |
| *A23B 4/24* | (2006.01) | |
| *C11D 11/00* | (2006.01) | |
| *A23B 4/30* | (2006.01) | |
| *A01N 59/00* | (2006.01) | |

(52) U.S. Cl.
CPC ............ *A22C 21/0061* (2013.01); *A23B 4/20* (2013.01); *A23B 4/24* (2013.01); *A23B 4/30* (2013.01); *A23L 3/3508* (2013.01); *A23L 3/358* (2013.01); *A23L 3/3526* (2013.01); *C11D 3/48* (2013.01); *C11D 11/0041* (2013.01); *C11D 17/0008* (2013.01)

(58) Field of Classification Search
CPC ...... A23L 3/3508; A23L 3/3526; A23L 3/358; A61L 2/16; C11D 3/48; C11D 7/28; C11D 11/0041; C11D 17/0008
See application file for complete search history.

(56) References Cited

U.S. PATENT DOCUMENTS

| | | |
|---|---|---|
| 4,373,075 A | 2/1983 | Schwarz |
| 4,944,068 A | 7/1990 | Covell, III |
| 5,384,102 A | 1/1995 | Ferguson et al. |
| 5,395,625 A | 3/1995 | Tang |
| 5,427,748 A | 6/1995 | Wiedrich et al. |
| 5,575,923 A | 11/1996 | Solomon et al. |
| 5,587,083 A | 12/1996 | Twardowski |
| 5,707,739 A | 1/1998 | Wellinghoff et al. |
| 5,960,808 A | 10/1999 | Ferguson et al. |
| 6,117,316 A | 9/2000 | Burton |
| 6,138,703 A | 10/2000 | Ferguson et al. |
| 6,227,463 B1 | 5/2001 | Porter |
| 6,238,643 B1 | 5/2001 | Thangaraj et al. |
| 6,298,871 B1 | 10/2001 | Pickens et al. |
| 6,438,703 B1 | 8/2002 | Beming et al. |
| 6,517,727 B2 | 2/2003 | Pickens et al. |
| 6,544,487 B1 | 4/2003 | Ferguson et al. |
| 6,605,253 B1 | 8/2003 | Perkins |
| 6,852,238 B2 | 2/2005 | Connelly, Jr. |
| 7,081,232 B1 | 7/2006 | Dooley, Jr. et al. |
| 7,090,882 B2 | 8/2006 | Koefod et al. |
| 7,309,444 B2 | 12/2007 | Connelly, Jr. |
| 7,431,863 B2 | 10/2008 | Pickens |
| 7,462,289 B2 | 12/2008 | Ayats et al. |
| 7,488,457 B2 | 2/2009 | DiMascio |
| 7,534,368 B2 | 5/2009 | Martin |
| 7,682,513 B2 | 3/2010 | Wang |
| 7,927,508 B2 | 4/2011 | Martin |
| 8,318,231 B2 | 11/2012 | Warf, Jr. et al. |
| 8,361,409 B2 | 1/2013 | Rico et al. |
| 2003/0059483 A1 | 3/2003 | Sowle et al. |
| 2004/0067160 A1 | 4/2004 | Perkins |
| 2004/0253352 A1 | 12/2004 | Koefod et al. |
| 2005/0013878 A1* | 1/2005 | Mingzhong ............ A01N 59/00 424/722 |
| 2006/0191833 A1 | 8/2006 | Green, III et al. |
| 2007/0042094 A1 | 2/2007 | Warf, Jr. et al. |
| 2007/0202095 A1 | 8/2007 | Speronello et al. |
| 2007/0295936 A1 | 12/2007 | Byrne et al. |
| 2008/0031805 A1 | 2/2008 | Bergmann et al. |
| 2008/0047897 A1 | 2/2008 | Jeong et al. |
| 2010/0108581 A1 | 5/2010 | Johnston et al. |
| 2011/0309297 A1 | 12/2011 | Thangaraj et al. |
| 2012/0145618 A1 | 6/2012 | Kuennen et al. |
| 2012/0276222 A1 | 11/2012 | Harvey et al. |
| 2013/0020265 A1 | 1/2013 | Kamatsuchi et al. |
| 2014/0308371 A1 | 10/2014 | Parasida et al. |

FOREIGN PATENT DOCUMENTS

| | | |
|---|---|---|
| WO | 2007023481 A1 | 3/2007 |
| WO | 2010137579 A1 | 12/2010 |
| WO | 2011070983 A1 | 6/2011 |
| WO | 2016118382 A1 | 7/2016 |

\* cited by examiner

METHOD OF SANITIZING A SURFACE

CROSS REFERENCE TO RELATED APPLICATION

This patent application is entitled to and claims the benefit of U.S. Provisional Patent Application No. 62/379,305, filed on Aug. 25, 2016, the disclosure of which is incorporated herein by reference in its entirety.

FIELD OF THE INVENTION

The present invention relates to a method of sanitizing a surface that includes contacting a first feed aqueous stream with a pH control composition so as to form a first treated aqueous stream, combining at least a portion of the first treated aqueous stream with a feed sanitizing aqueous stream that includes free available halogen, thereby forming a treated sanitizing aqueous stream that includes free available halogen, heating the treated sanitizing aqueous stream, and applying the resulting heated treated sanitizing aqueous stream to a surface to be sanitized.

BACKGROUND OF THE INVENTION

In the processing of foods, such as fruits, vegetables, and animal carcasses, the food surfaces and related processing equipment surfaces are typically cleaned before, during, and after processing of the foods, such as with water. The food surfaces and related processing equipment are, in some situations, treated with water that includes a non-halogen sanitizing agent, such as peroxyacetic acid. The use of halogen sanitizing agents is avoided when cleaning food and/or food processing surfaces, in some situations, due to concerns relating to corrosion of equipment and controlling the level of free halogen so as to provide both at least sufficient sanitizing properties and minimal residual free halogen on the treated surfaces. Halogen sanitizing agents can be effective with regard to the reduction of microorganisms, including pathogens.

It would be desirable to develop new methods of sanitizing surfaces, such as the surfaces of animal carcasses, that involve the use of halogen sanitizing agents.

SUMMARY OF THE INVENTION

In accordance with the present invention, there is provided a method of sanitizing a surface that comprises, (a) providing a pH control composition comprising at least one pH control agent, and (b) contacting a first feed aqueous stream with said pH control composition, thereby forming a first treated aqueous stream. The method of the present invention further comprises, (c) combining at least a portion of the first treated aqueous stream with a feed sanitizing aqueous stream comprising free available halogen, thereby forming a treated sanitizing aqueous stream comprising free available halogen. The method of the present invention additionally comprises, (d) elevating the temperature of the treated sanitizing aqueous stream, thereby forming a heated treated sanitizing aqueous stream having an elevated temperature, and (e) applying said heated treated sanitizing aqueous stream to a surface to be sanitized.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1 through 3, which are not to scale, like reference characters designate the same components and structural features.

DETAILED DESCRIPTION OF THE INVENTION

Figure 1:
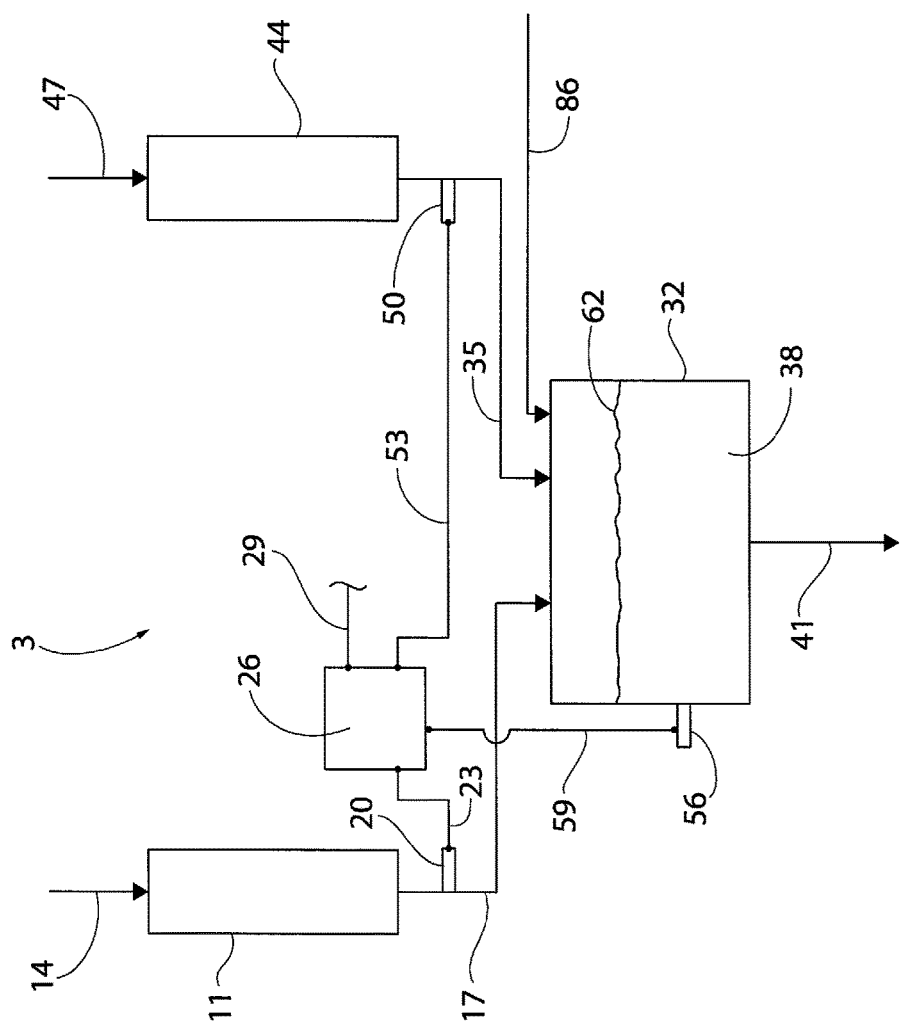
FIG. 1 is a schematic representation of a water treatment system that can be used with a method according to the present invention.

As used herein, spatial or directional terms, such as "left", "right", "inner", "outer", "above", "below", and the like, relate to the invention as it is shown in the drawing figures. However, it is to be understood that the invention can assume various alternative orientations and, accordingly, such terms are not to be considered as limiting.

Unless otherwise indicated, all numbers expressing quantities of ingredients, reaction conditions, processing parameters, physical characteristics, dimensions, and the like used in the specification and claims are to be under stood as modified in all instances by the term "about."

Unless otherwise indicated, all ranges or ratios disclosed herein are to be understood to encompass any and all subranges or subratios subsumed therein. For purposes of non-limiting illustration, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 3.3, 4.7 to 7.5, 5.5 to 10, and the like.

As used herein, the articles "a," "an," and "the" include plural referents unless otherwise expressly and unequivocally limited to one referent.

As used herein, the term "sanitizing" means reducing microorganisms and/or reducing the activity of microorganisms at least to levels considered to be safe, such as by applicable public health codes and/or regulations, without adversely affecting the quality and/or the safety of the surface that is sanitized.

As used herein, the term "alkali metal" means one or more of the alkali metals of the periodic table of the elements, such as lithium, sodium, potassium, rubidium, and cesium. As used herein, the term "alkaline earth metal" means one or more of the alkaline earth metals of the periodic table of the elements, such as beryllium, magnesium, calcium, strontium, barium, and radium.

All documents, such as but not limited to issued patents and patent applications, referred to herein, and unless otherwise indicated, are to be considered to be "incorporated by reference" in their entirety.

With some embodiments of the present invention, the elevated temperature of the heated treated sanitizing aqueous stream is at least 37° C. (98° F.) and less than 100° C. (212° C.). With some further embodiments of the present invention, the elevated temperature of the heated treated sanitizing aqueous stream is at least 37° C. (98° F.) and less than or equal to 66° C. (151° F.). With some further embodiments of the present invention, the elevated temperature of the heated treated sanitizing aqueous stream is at least 37° C. (98° F.) and less than or equal to 60° C. (140° F.). With some further embodiments of the present invention, the elevated temperature of the heated treated sanitizing aqueous stream is at least 37° C. (98° F.) and less than or equal to 54° C. (130° F.).

The temperature of the treated sanitizing aqueous stream can be elevated in accordance with art-recognized methods. With some embodiments, the temperature of the treated sanitizing aqueous stream is elevated by combining it with a third feed aqueous stream that is heated, as discussed in further detail herein. With some further embodiments, the temperature of the treated sanitizing aqueous stream is elevated by passing it through or in contact with a heat exchanger.

The heated treated sanitizing aqueous stream, with some embodiments, is applied to the surface to be sanitized by an application method selected from, for example, wiping, immersion, curtain application, spray application, and combinations of two or more such application methods.

In accordance with some embodiments of the present invention, the surface to be sanitized is selected from vegetable surfaces, fruit surfaces, equipment surfaces, animal carcass surfaces, and combinations of two or more such surfaces. Examples of animal carcasses, the surfaces of which can be treated in accordance with the method of the present invention, include, but are not limited to, fowl carcasses (such as poultry carcasses), beef carcasses, and pork carcasses.

The surface that is sanitized, with some embodiments of the method of the present invention, is selected from poultry carcass surfaces and/or poultry processing equipment surfaces. Examples of poultry, the poultry carcass surfaces of which can be treated with some embodiments of the present invention, include, but are not limited to, game hens (such as Cornish game hens), chickens, turkeys, pheasants, grouse, ducks, and geese. With some embodiments of the present invention, poultry carcass surfaces that are sanitized include, chicken carcass surfaces, turkey carcass surfaces, duck carcass surfaces, and geese carcass surfaces.

Examples of poultry processing equipment, the surfaces of which can be sanitized with some embodiments of the present invention, include, but are not limited to, poultry picking rails, poultry picking (or plucking) fingers, poultry picking finger drums (e.g., the drums that the poultry picking fingers are attached to), and poultry cutting tables (such as, metal tables on which the poultry are cut up into separate pieces).

With some embodiments of the present invention, the heated treated sanitizing aqueous stream is concurrently contacted with: (i) the poultry picking fingers and poultry picking drum(s); and (ii) the poultry carcass surfaces, while the poultry carcass is being plucked by the poultry picking fingers of the poultry picking drum.

The heated treated sanitizing aqueous stream is applied to poultry carcass surfaces, with some embodiments of the present invention, by at least partial immersion of the poultry carcass surface in a poultry scalder. With some embodiments, the poultry carcasses are at least partially immersed in the poultry scalder after evisceration of the poultry and prior to removal of the feathers from the poultry carcasses. At least partial immersion in the poultry scalder serves, with some embodiments of the present invention, to assist with removal of at least some of the feathers from the poultry carcasses.

The heated treated sanitizing aqueous stream is introduced into the poultry scalder, and then the poultry carcasses are at least partially immersed in the poultry scalder, which results in application of the heated treated sanitizing aqueous stream to the poultry carcass surfaces, with some embodiments of the present invention. With some embodiments of the present invention, the heated treated sanitizing aqueous stream is introduced into the poultry scalder under batch conditions, intermittently, or continuously.

The heated treated sanitizing aqueous stream is circulated in the poultry scalder countercurrent to the movement of the poultry carcasses as they pass through the poultry scalder, with some embodiments of the present invention. With some embodiments of the present invention, the poultry carcasses are at least partially immersed in the heated treated sanitizing aqueous stream within the poultry scalder while hanging downward by their legs and/or feet from a picking rail that conveys the poultry carcasses through the poultry scalder. With some further embodiments, the poultry carcasses are dumped into the poultry scalder and the surfaces thereof are contacted with the heated treated sanitizing aqueous stream for a predetermined period of time, followed by removal of the poultry carcasses from the poultry scalder, such as with perforated ladles or hooks, or by draining the heated treated sanitizing aqueous stream from the poultry scalder and then removing the poultry carcasses therefrom.

The method of the present invention further includes, with some embodiments, optionally rinsing the surface that has been sanitized by contact with the heated treated sanitizing aqueous stream (the sanitized surface). With some embodiments, the sanitized surface is rinsed with an aqueous rinsing composition that includes water and which has a low free available halogen content, such as a free available halogen content that is less than or equal to 1 ppm. The aqueous rinsing composition can optionally include, with some embodiments, one or more additives including, but not limited to, surfactants and/or inorganic salts. Rinsing of the sanitized surface is undertaken, with some embodiments, for reasons including, but not limited to, reducing the level of free available halogen that may be present on the sanitized surface, such as to a level that is less than or equal to 1 ppm.

The pH control agent of the pH control composition, with some embodiments, includes an inorganic acid, an inorganic acid salt, an organic acid, and/or an organic acid salt. Nonlimiting examples of inorganic acids include hydrogen halides and sulfuric acid. Nonlimiting examples of inorganic acid salts include alkali metal salts of sulfuric acid, such as alkali metal bisulfate, alkaline earth metal salts of sulfuric acid, such as alkaline earth metal sulfate. Examples of organic acids include, but are not limited to, carbonic acid, and carboxylic acids (such as hydrocarbyl carboxylic acids, including, but not limited to, linear or branched alkyl carboxylic acids, cycloalkyl carboxylic acids, and aromatic carboxylic acids). Examples of salts of organic acids include, but are not limited to, alkali metal salts and alkaline earth metal salts of the previously recited classes and sub-classes of organic acids.

The pH control agent of the pH control composition includes, which some embodiments, at least one of a bisulfate salt, a carbonate salt, a bicarbonate salt, a carboxylic acid, a carboxylic acid salt, carbonic acid, and a hydrogen halide. Nonlimiting examples of bisulfate salts include alkali metal bisulfates (such as, sodium bisulfate and potassium bisulfate), alkali earth metal bisulfates (such as, magnesium bisulfate). Examples of carbonate salts include, but are not limited to, alkali metal carbonate (such as, sodium carbonate and potassium carbonate). Examples of bicarbonate salts include, but are not limited to, alkali metal bicarbonates (such as, sodium bicarbonate and potassium bicarbonate) and alkaline earth metal bicarbonates (such as, calcium bicarbonate and magnesium bicarbonate). Examples of carboxylic acids include, but are not limited to, hydrocarbyl carboxylic acids having one or more carboxylic acid groups (such as, linear $C_1$-$C_{20}$ alkyl carboxylic acids, branched $C_3$-$C_{20}$ alkyl carboxylic acids, $C_5$-$C_8$ cycloalkyl carboxylic acids, and aromatic carboxylic acids having at least 6 carbons in the aromatic ring, in each case independently having one or more carboxylic acid groups). Examples of hydrocarbyl carboxylic acids having more than one carboxylic acid group include, but are not limited to, citric acid and succinic acid. Examples of carboxylic acid salts include, but are not limited to alkali metal salts and alkaline earth metal salts of the previously recited classes and sub-classes of hydrocarbyl carboxylic acids. Carbonic acid can be formed, with some embodiments, by dissolving carbon dioxide in an aqueous system, such as water. Examples of hydrogen halides include, but are not limited to, hydrogen chloride (HCl), hydrogen bromide (HBr), and hydrogen iodide (HI).

The pH control agent includes, with some embodiments, at least one bisulfate salt selected from alkali metal bisulfate, alkaline earth metal bisulfate, and combinations thereof.

With some embodiments of the present method, the pH control agent includes at least one alkali metal bisulfate, such as sodium bisulfate, potassium bisulfate, and/or lithium bisulfate. As used herein the term "alkali metal bisulfate" and the term "alkali hydrogen sulfate" are equivalent terms.

In accordance with some embodiments of the method of the present invention, the pH control agent includes at least one alkali metal bisulfate anhydrous, such as sodium bisulfate anhydrous, potassium bisulfate anhydrous, and/or lithium bisulfate anhydrous. As used herein the term "alkali metal bisulfate anhydrous" and "alkali metal hydrogen sulfate anhydrous" are equivalent terms.

The alkali metal bisulfate anhydrous (alkali metal hydrogen sulfate anhydrous), with some embodiments, contains water in an amount of 0 percent by weight to 1 percent by weight, or from 0 percent by weight to 0.5 percent by weight, or from 0 percent by weight to 0.2 percent by weight, or from 0 percent by weight to 0.1 percent by weight, the percent weights being based on the weight of the alkali metal bisulfate anhydrous (alkali metal hydrogen sulfate anhydrous).

The alkali metal bisulfate material can be in any suitable form. With some embodiments, the alkali metal bisulfate material is in the form of a solid particulate material. In accordance with some further embodiments, the alkali metal bisulfate material is in the form of a solid particulate material having an average particle size of from 25 microns to 1000 microns, or 50 microns to 1000 microns, or 100 microns to 1000 microns, or 150 microns to 1000 microns, or 200 microns to 1000 microns, or from 250 microns to 800 microns, or from 300 microns to 700 microns, or from 400 microns to 600 microns.

The alkali metal of the alkali metal bisulfate is, with some embodiments, selected from any suitable alkali metal, such as, but not limited to, lithium, sodium, and potassium. In accordance with some embodiments, the alkali metal of the alkali metal bisulfate is selected from sodium and potassium. The alkali metal bisulfate is, with some further embodiments, selected from sodium bisulfate, sodium bisulfate anhydrous, and combinations thereof. With some further embodiments, the alkali metal bisulfate is sodium bisulfate.

In accordance with some embodiments, the alkali metal bisulfate is present in the pH control composition in an amount of about 50 percent by weight to about 100 percent by weight, or about 75 percent by weight to about 99 percent by weight, or about 80 percent by weight to 95 percent by weight, or about 88 percent by weight to about 92 percent by weight, or about 88.5 percent by weight to about 91.5 percent by weight, or about 89 percent by weight to about 91 percent by weight, the percent weights being based on total weight of the pH control composition.

The pH control compositions of the method of the present invention further include, with some embodiments, one or more colorants. Each colorant can, with some embodiments, be independently selected from one or more dyes, one or more pigments, and combinations thereof. Examples of dyes from which the colorant can be selected, with some embodiments, include, but are not limited to, dyes having the following US Food and Drug Administration designations: FD&C Blue No. 1, FD&C Blue No. 2, FD&C Green No. 3, FD&C Red No. 40, FD&C Red No. 3, FD&C Yellow No. 5, FD&C Yellow No. 6, and combinations of two or more thereof. Examples of pigments from which the colorant can be selected, with some embodiments, include, but are not limited to, inorganic pigments, organic pigments, and combinations thereof. Examples of inorganic pigments include, but are not limited to, carbon blacks, and transition metal oxides, such as, titanium dioxide and iron oxides, such as red iron oxide, black iron oxide, and yellow iron oxide. Examples of organic pigments include, but are not limited to: quinacridones; phthalocyanines, such as phthalo green and phthalo blue; naphthols, such as naphthol red; and anthracenes, such as anthracene-9,10-diones, including for example pigments derived from carminic acid, such as carmine.

With some embodiments, the colorant includes carmine. In accordance with some further embodiments, the colorant is carmine.

With some embodiments, the colorant is a food grade colorant, which has been approved by a government body, such as the US Food and Drug Administration for use in foods. Examples of food grade colorants include, but are not limited to, FD&C Blue No. 1, FD&C Blue No. 2, FD&C Green No. 3, FD&C Red No. 40, FD&C Red No. 3, FD&C Yellow No. 5, FD&C Yellow No. 6, and combinations of two or more thereof.

The colorant, with some embodiments, is present in any suitable amount that provides a desired color to the pH control composition (which can be in the form of a tablet, as discussed further herein). The colorant is present, with some embodiments, for purposes of providing the pH composition and/or tablet thereof with a color that allows it to be visually distinguishable from other compositions and tablets, such as other water treatment compositions and tablets, such as calcium hypochlorite compositions and calcium hypochlorite tablets, 1,3,5-trichloro-1,3,5-triazine-2,4,6-trione (also known as trichloro-s-triazinetrione) compositions and tablets, and bromochlorodimethylhydantoin compositions and tablets.

With some embodiments, the colorant is present in an amount of less than or equal to 10 percent by weight (or up to 10 percent by weight), or less than or equal to 5 percent by weight (or up to 5 percent by weight), or less than or equal to 1 percent by weight (or up to 1 percent by weight) based on the total weight of the pH control composition. In accordance with some further embodiments, the colorant is present in an amount of 0.001 percent by weight to 10 percent by weight, or 0.003 percent by weight to 5 percent by weight, or 0.004 percent by weight to 1 percent by weight, or from 0.005 percent by weight to 0.5 percent by weight, or from 0.006 percent by weight to 0.3 percent by weight, based on the total weight of the pH control composition. In accordance with some additional embodiments, the colorant is present in an amount of less than or equal to 0.0075 percent by weight (or up to 0.0075 percent by weight) such as from 0.001 percent by weight to 0.0075 percent by weight, based on the total weight of the pH control composition.

The pH control compositions of the present invention can, in accordance with some embodiments, optionally include a binder, such as, but not limited to, one or more polysaccharide binders, one or more polyvinylpyrrolidone binders, one or more polyvinyl acetate binders, one or more polyalkylene glycol ether binders, and/or one or more alkaline earth metal carboxylate binders. Examples of polysaccharide binders include, but are not limited to, methyl cellulose binders, hydroxyl propyl cellulose binders, starch binders, sodium alginate binders, and xantham binders. Examples of polyalkylene glycol ether binders include, but are not limited to, polyethylene glycol ether binders, polypropylene glycol ether binders, and poly(ethylene glycol ether propylene glycol ether) binders. Examples of alkaline earth metal carboxylate binders include, but are not limited to, alkaline earth metal salts of fatty carboxylic acids, such as calcium stearate and magnesium stearate.

The binder can be present in any suitable amount. With some embodiments of the present invention, the pH composition includes a binder in an amount of from 0.001 percent by weight to 5 percent by weight, or from 0.005 percent by weight to 3 percent by weight, or from 0.01 percent by weight to 2 percent by weight, the percent weights being based on the total weight of the pH control composition.

The pH control composition can be in liquid or solid form at ambient temperatures, such as 25° C., with the method of the present invention. With some embodiments of the present invention, the pH control composition is an aqueous pH control composition that includes water and one or more pH control agents.

The pH control composition used in the method of the present invention, with some embodiments, is in the form of a tablet. When in tablet form, the pH control compositions of the method of the present invention are referred to herein as a "pH control tablet composition(s)" or a "pH control tablet(s)."

As used herein, the term "tablet" means a three-dimensionally shaped object that is composed of the pH control composition of the present invention and which is self-supporting.

With some embodiments, the pH control tablets of the present invention have any desirable shape and dimension. The pH control tablets of the present invention have, with some further embodiments, a disk-like shape with: a height of from 15 to 50 mm, or from 20 to 40 mm, or from 22 to 35 mm, such as 28 mm; and a diameter of from 3 to 10 cm, or from 4 to 8 cm, or from 5 to 7 cm, such as 6.7 cm.

The pH control tablets of the method of the present invention, with some embodiments, have a density of from 1.8 to 2.2 g/cm$^3$, or from 1.80 to 2.20 g/cm$^3$, or from 2.0 to 2.1 g/cm$^3$, or from 2.00 to 2.10 g/cm$^3$, or from 2.01 to 2.08 g/cm$^3$, or from 2.02 to 2.05 g/cm$^3$.

The pH control tablets of the method of the present invention have, with some embodiments, a moisture absorption of less than 10 percent by weight, such as from 1 to 10 percent by weight, or from 2 to 9 percent by weight, or from 5 to 8.5 percent by weight, based on the initial weight of the tablet (such as prior to exposure to moisture). The moisture absorption is determined, with some embodiments, by suspending a pH control tablet at room temperature (such as 25° C.) above water in a closed container for 200 hours. The pH control tablet is weighed periodically, such as daily, during the course of the test, and the weight of the pH control tablet is compared to that of the pH control tablet prior to being placed in the container, and the percent weight of water absorption is calculated from such comparison. In accordance with some embodiments, the pH control tablets of the method of the present invention have a moisture absorption of from 5 to 8.5 percent by weight, such as 8.1 percent by weight, and are substantially free of crumbling, as determined by subjecting the pH control tablet to torsional and flexural stresses by human hands.

The pH control tablets of the method of the present invention can be formed, with some embodiments, by mixing (such as dry mixing) together the components thereof, such as the alkali metal hydrogen sulfate, optional colorant, and optional binder to form a substantially homogenous composition. The substantially homogenous composition is, with some embodiments, placed in a mold, such as a metal mold, such as a stainless steel mold, and subjected to elevated pressure for a period of time. The elevated pressure can, with some embodiments, be at least 10,000 pounds per square inch (psi), such as from 10,000 to 30,000 psi, or from 15,000 to 25,000 psi, such as, 22,000 psi. The tablet mold is opened, and the pH control tablet is removed therefrom.

In accordance with the method of the present invention, formation of the first treated aqueous stream involves contacting a first feed aqueous stream with the pH control composition, as described previously herein. The first treated aqueous stream can be formed as a batch process or as a continuous process.

The first treated aqueous stream can be formed remotely, such as at a remote facility, relative to the place (or facility) where it is combined with the feed sanitizing aqueous stream, with some embodiments of the present method. For purposes of non-limiting illustration, the first treated aqueous stream can be formed by contacting the first feed aqueous stream with the pH control composition at a first facility. The first treated aqueous stream can then be transported from the first facility by suitable transportation means, such as in tanker trucks, drums, or through a pipe line, to a second facility where the first treated aqueous stream is combined with the feed sanitizing aqueous stream, so as to form the treated sanitizing aqueous stream, with some embodiments of the method of the present invention.

The first feed aqueous stream includes, with some embodiments, water. With some embodiments, the first feed aqueous stream is drawn from an untreated fresh water source, such as untreated well water, untreated river water, untreated lake water, untreated cistern water, and combinations thereof. The first feed aqueous stream, with some further embodiments, is drawn from a treated, such as sanitized, fresh water source, such as treated well water, treated river water, treated lake water, treated cistern water, and city water. At least a portion of the first feed aqueous stream can include reuse water. The term "reuse water" as used herein means water that has been used in a separate process, process step, and/or station, such as a rinsing process, rinsing process step, and/or rinsing station. The reuse water is typically treated, such as sanitized, before use as at least part of the first feed aqueous stream, with some embodiments of the present invention.

In accordance with some embodiments of the method of the present invention, the first treated aqueous stream has a pH that is lower than (or less than) the pH of the first feed aqueous stream. In accordance with some further embodiments, the first treated aqueous stream has a pH of less than or equal to 8, such as less than or equal to 7.5, such as less than or equal to 7, or from 1 to 8, or from 1 to 7.5, or from 2 to 7, or from 3 to 6.5, or from 4 to 6. With some embodiments, the first treated aqueous stream has a pH of from 6 to 8, or from 6 to 7.5, or from 6 to 7.

The first feed aqueous stream can be contacted with the pH control composition in any suitable manner. With some embodiments, the pH control composition of the present method is contained in a container and the first feed aqueous stream is introduced into the container. The introduced first feed aqueous stream is, with some batch embodiments, held in the container for a period of time, and then at least a portion thereof removed from the container as the first treated aqueous stream. The first feed aqueous stream is, with some continuous embodiments, introduced continuously into the container, and the first treated aqueous stream is removed continuously from the container.

For purposes of non-limiting illustration and with reference to FIG. 1, the water treatment system 3 includes a first feeder unit 11 that contains the pH control tablets of the method of the present invention (not visible in FIG. 1). A first feed aqueous stream is introduced into the first feeder unit 11 as indicated by arrow 14, which also represents a conduit 14. The first feed aqueous stream and the pH control tablets are contacted together within first feeder unit 11. A first treated aqueous stream is withdrawn from first feeder unit 11 as indicated by arrow 17, which also represents a conduit 17. The pH of the first treated aqueous stream passing through conduit 17 is measured by a suitable probe, such as probe 20. The pH output signals of probe 20 are relayed to a processor unit 26 by electrical connection 23. Processor unit 26 can be connected to an external power source, not shown, by electrical connection 29. Depending on the pH values transmitted to processor unit 26, the amount and rate of the first feed aqueous stream 14 introduced into first feeder unit 11 and/or the amount and rate of first treated aqueous stream 17 removed from first feed unit 11 can be adjusted by one or more valves, such as remotely controlled valves, not shown. With some embodiments, a portion of the first treated aqueous stream passing through conduit 17 can be diverted, such as through a separate conduit (not shown) so as to be used alone. Examples of such sole use of the first treated aqueous stream alone include, but not limited to: application to a surface, such as equipment surfaces and/or food surfaces, for purposes of cleaning the surface.

The method of the present invention further includes combining at least a portion of the first treated aqueous stream with a feed sanitizing aqueous stream that includes free available halogen, thereby forming the treated sanitizing aqueous stream that includes free available halogen.

The first treated aqueous stream and the feed sanitizing aqueous stream can be combined by any suitable method or methods. With some embodiments, the first treated aqueous stream and the feed sanitizing aqueous stream are combined together in a mixing tank, such as in accordance with the non-limiting embodiments as described further herein with reference to FIG. 1. The first treated aqueous stream and the feed sanitizing aqueous stream are combined together, with some embodiments, by introducing the first treated aqueous stream into a conduit carrying the feed sanitizing aqueous stream, such as in accordance with the non-limiting embodiments as described further herein with reference to FIG. 2. The first treated aqueous stream and the feed sanitizing aqueous stream are combined together, with some further embodiments, by introducing the feed sanitizing aqueous stream into a conduit carrying the first treated aqueous stream, not depicted in the drawings. The first treated aqueous stream and the feed sanitizing stream are combined together, with some additional embodiments, by introducing the first treated aqueous stream and the feed sanitizing aqueous stream into a conduit carrying a primary aqueous stream, such as in accordance with the non-limiting embodiments as described further herein with reference to FIG. 3.

The term "free available halogen" as used herein means halogen that is present in an oxidized form in an aqueous solution, such as the feed sanitizing aqueous stream, the treated sanitizing aqueous stream, and the heated treated sanitizing aqueous stream. Free available halogen (FAH) is present in the form of hypohalous acid (HOX) and/or hypohalite anion ($XO^-$), wherein X represents a halogen group having a +1 oxidation state. The halogen, X, of the free available halogen is selected from chlorine, bromine and iodine, with some embodiments.

The free available halogen of the feed sanitizing aqueous stream, the treated sanitizing aqueous stream, and the heated treated sanitizing aqueous stream, with some embodiments, includes free available chlorine, free available bromine, or free available iodine. With some embodiments, the free available halogen of the feed sanitizing aqueous stream, the treated sanitizing aqueous stream, and the heated treated sanitizing aqueous stream includes, or is, free available chlorine. With some further embodiments of the method of the present invention, the feed sanitizing aqueous stream, the treated sanitizing aqueous stream, and the heated treated sanitizing aqueous stream each independently include free available chlorine.

The amount of free available halogen present in the feed sanitizing aqueous stream, the treated sanitizing aqueous stream, and the heated treated sanitizing aqueous stream can vary, provided that, with some embodiments, the heated treated sanitizing aqueous stream includes at least a sufficient amount of free available halogen such that it can be used to clean and/or sanitize one or more surfaces to which it is applied. With some embodiments, the amount of free available halogen in each of the treated sanitizing aqueous stream and the heated treated sanitizing aqueous stream is less than the amount of free available halogen present in the feed sanitizing aqueous stream, because the first treated aqueous stream is combined with the feed sanitizing aqueous stream, thereby resulting in a reduced or diluted amount of free available halogen within the resulting treated sanitizing aqueous stream and correspondingly the heated treated sanitizing aqueous stream.

With some embodiments, the amount of free available halogen present in the treated sanitizing aqueous stream and the heated treated sanitizing aqueous stream is in each case independently from 0.001 percent to 99.9 percent less than, or from 10 percent to 90 percent less than, or from 25 percent to 75 percent less than the amount of free available halogen present in the feed sanitizing aqueous stream.

The amount of free available halogen present in the treated sanitizing aqueous stream, the heated treated sanitizing aqueous stream, and the feed sanitizing aqueous stream are, with some embodiments, is in each case independently from 10 ppm to 100,000 ppm, or from 30 ppm to 30,000 ppm, or from 50 to 20,000 ppm, or from 50 ppm to 5000 ppm, or from 50 ppm to 1000 ppm, or from 50 to 500 ppm; provided that, with some further embodiments, the amount of free available halogen present in the treated sanitizing aqueous stream and the heated treated sanitizing aqueous stream is in each case lower than the amount of free available halogen present in the feed sanitizing aqueous stream. With some embodiments, the amount of free available halogen present in the treated sanitizing aqueous stream is at least 1 ppm, such as from 1 ppm to 1000 ppm, or from 1 ppm to 500 ppm, or from 10 ppm to 450 ppm, or from 30 ppm to 50 ppm. With some additional embodiments, the amount of free available halogen present in the heated treated sanitizing aqueous stream is at least 1 ppm, such as from 1 ppm to 1000 ppm, or from 1 ppm to 500 ppm, or from 10 ppm to 450 ppm, or from 30 ppm to 50 ppm.

The treated sanitizing aqueous stream and the heated treated sanitizing aqueous stream each independently have a pH of 6 to 8, or 6 to 7.5, or 6 to 7, with some embodiments of the present invention. With some further embodiments: the free available halogen of the treated sanitizing aqueous stream and the heated treated sanitizing aqueous stream each independently include free available chlorine; and the treated sanitizing aqueous stream and the heated treated sanitizing aqueous stream, each independently have a pH of 6 to 8, or 6 to 7.5, or 6 to 7.

The feed sanitizing aqueous stream, in accordance with some embodiments, is formed by contacting a second feed aqueous stream with a source of free available halogen. The source of free available halogen releases free available halogen into the second feed aqueous stream, thereby resulting in formation of the feed sanitizing aqueous stream.

The source of free available halogen, with some embodiments, is selected from calcium hypochlorite, sodium hypochlorite, potassium hypochlorite, lithium hypochlorite, chlorine gas, 1,3,5-trichloro-1,3,5-triazine-2,4,6-trione, 1-bromo-3-chloro-5,5-dimethylhydantoin, and combinations thereof.

The first and second feed aqueous streams each independently include water, with some embodiments. With some further embodiments, the first and second feed aqueous streams are each independently drawn from an untreated fresh water source, such as untreated well water, untreated river water, untreated lake water, untreated cistern water, and combinations thereof. The first and second feed aqueous streams, with some additional embodiments, are each independently drawn from a treated, such as sanitized, fresh water source, such as treated well water, treated river water, treated lake water, treated cistern water, and city water. The first and second feed aqueous streams are, with some embodiments, drawn from the same or different sources. The first and second feed aqueous streams are the same or different, with some embodiments.

The first feed aqueous stream (used to form the first treated aqueous stream), the second feed aqueous stream (used to form the feed sanitizing aqueous stream), and the treated sanitizing aqueous stream, each independently have a temperature, with some embodiments of the present invention, that is less than the elevated temperature of the heated treated sanitizing aqueous stream. With some embodiments, the first feed aqueous stream, the second feed aqueous stream, and the treated sanitizing aqueous stream each independently have a temperature of less than 37° C. (98° F.), such as from 4.4° C. (40° F.) to 24° C. (75° F.), or from 10° C. (50° F.) to 18.3° C. (65° F.).

In accordance with some embodiments of the present invention, for purposes of non-limiting illustration, and with reference to the water treatment system 3 of FIG. 1, one or more pH control tablets are contained within first feeder unit 11. A first feed aqueous stream is introduced into first feeder unit 11 as indicated by arrow 14, which also represents a conduit 14. The first feed aqueous stream and the pH control tablet(s) are contacted with each other within first feeder unit 11. A first treated aqueous stream is formed in and withdrawn from first feeder unit 11 as indicated by arrow 17, which also represents a conduit 17.

The first treated aqueous stream is forwarded through conduit 17 and into mixing tank 32 where it is combined with a feed sanitizing aqueous stream that has been forwarded through conduit 35 into mixing tank 32. Mixing tank 32 can include one or more dynamic mixers, such as one or more impellers, not shown. A treated sanitizing aqueous stream 38 is accordingly formed within mixing tank 32. The treated sanitizing aqueous stream 38 is removed and forwarded from mixing tank 32 through conduit 41. The treated sanitizing aqueous stream 38 can be held within mixing tank 32 and intermittently released from mixing tank 38 through conduit 41. Alternatively, the treated sanitizing aqueous stream 38 can be continuously removed from mixing tank 32 and continuously forwarded through conduit 41 as the sanitizing aqueous stream 38 is formed within mixing tank 32.

With some embodiments, the temperature of the treated sanitizing aqueous stream formed in mixing tank 32 can be elevated, so as to form the heated treated sanitizing aqueous stream by methods that include, but are not limited to: (i) heating the treated sanitizing aqueous stream within mixing tank 32 by a heat exchanger immersed therein and/or a heat exchanger in contact with the exterior of mixing tank 32 (in each case not shown); (ii) forwarding the treated sanitizing aqueous stream formed in mixing tank 32 through conduit 41 to a heat exchanger (not shown); and/or (iii) introducing a third feed aqueous stream that is heated into mixing tank 32 through conduit 86. The temperature of the heated treated sanitizing aqueous stream can be measured and controlled by art-recognized methods, such as by one or more appropriately placed thermocouples (not shown) that are in electrical communication with a processor unit (not shown) that is in electrical communication with one or more heat exchangers (not shown). Depending on the temperature values measured by the thermocouple(s), the amount of thermal energy introduced into the treated sanitizing aqueous stream can be appropriately adjusted, so as to result in the formation of a heated treated sanitizing aqueous stream that has a desired or target elevated temperature (or elevated temperature range).

With further reference to FIG. 1, the feed sanitizing aqueous stream is formed within second feeder unit 44. Second feeder unit 44 includes a source of free available halogen, such as calcium hypochlorite, which can be in the form of one or more calcium hypochlorite tablets (not shown). A second feed aqueous stream is introduced into second feeder unit 44 as indicated by arrow 47, which also represents a conduit 47. The second feed aqueous stream contacts the source of free available halogen within second feeder unit 44, which results in formation of the feed sanitizing aqueous stream that is removed from second feeder unit 44 and forwarded to mixing tank 32 through conduit 35.

The pH of the first treated aqueous stream can be measured as it passes through conduit 17 by probe 20 as described previously herein with regard to the treated aqueous stream. The pH and/or conductivity of the feed sanitizing aqueous stream passing through conduit 35 can be measured by probe 50. The pH and/or conductivity data measured by probe 50 are forwarded to processor unit 26 by electrical connection 53. Depending on the pH and/or conductivity values transmitted to processor unit 26 through electrical connection 53, the amount and rate of the second feed aqueous stream introduced into second feeder unit 44 through conduit 47 and/or the amount and rate of the feed sanitizing aqueous stream removed from second feed unit 44 through conduit 35 can be adjusted by one or more valves, such as remotely controlled valves, not shown.

The pH of the treated sanitizing aqueous stream 38 formed within mixing tank 32 can be measured by probe 56. Alternatively, or additionally, probe 56 can be placed in contact with conduit 41 so as to measure the pH of the treated sanitizing aqueous stream passing therethrough (not depicted in FIG. 1). The pH values measured by probe 56 are transmitted to processor unit 26 by electrical connection 59. Depending on the pH values transmitted to processor unit 26 through electrical connection 59, the amount and rate of the treated aqueous stream introduced into mixing tank 32 through conduit 17 and/or the amount and rate of the feed sanitizing aqueous stream introduced into mixing tank 32 through conduit 35 can be adjusted by one or more valves, such as remotely controlled valves, not shown. Depending on where in the process the heated treated sanitizing aqueous stream is formed, the pH thereof can be measured, with some embodiments, by one or more appropriately positioned probes (such as probe 56, if the heated treated sanitizing aqueous stream is formed within mixing tank 32).

With some embodiments, the level 62 of treated sanitizing aqueous stream 38 (or heated treated sanitizing aqueous stream) within mixing tank 32 can be measured by one or more probes (not shown) and transmitted to processor unit 26. The level 62 can be adjusted by adjusting the amount and rate of the treated aqueous stream introduced into mixing tank 32 through conduit 17, and/or adjusting the amount and rate of the feed sanitizing aqueous stream introduced into mixing tank 32 through conduit 35, and/or adjusting the amount and rate of treated sanitizing aqueous stream removed from mixing tank 32 through conduit 41 by one or more valves, such as remotely controlled valves, not shown.

In accordance with some embodiments, a third feed aqueous stream can be introduced and mixed or combined with the treated aqueous stream and the feed sanitizing aqueous stream. The third feed aqueous stream can be introduced for purposes including, but not limited to, adjusting the concentration of free available halogen present in the resulting treated sanitizing aqueous stream (such as by dilution) and/or elevating the temperature of the treated sanitizing aqueous stream (provided the third feed aqueous stream is heated and has an elevated temperature). The third feed aqueous stream can be selected from one or more of those sources as described previously herein with regard to the first and second feed aqueous streams, such as city water.

For purposes of non-limiting illustration, attention is directed to treatment system 3 of FIG. 1, in which a third feed aqueous stream is introduced into mixing tank 32 as indicated by arrow 86, which also represents a conduit 86, with some embodiments of the present invention. The rate and flow of the third feed aqueous stream introduced into mixing tank 32 can be controlled by one or more valves (not shown), which may be controlled by processor unit 26 in response to signals transmitted thereto by one or more probes in probing contact with conduit 86 (not shown).

Figure 2:
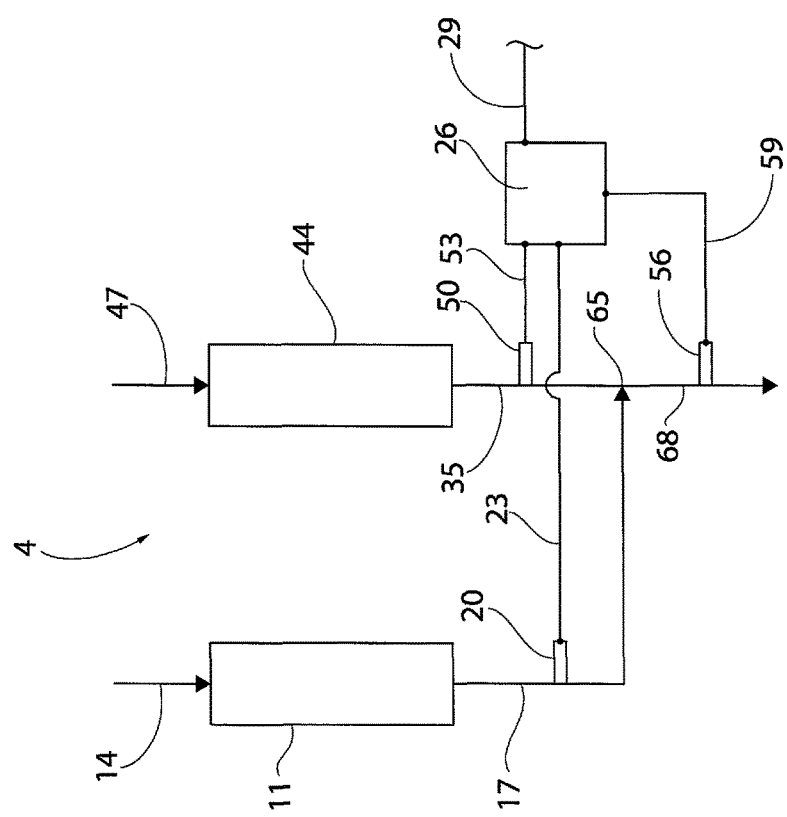
FIG. 2 is a schematic representation of another water treatment system that can be used with a method according to the present invention.

The method of forming a treated sanitizing aqueous stream with some embodiments of the present invention can be performed with the water treatment system 4 of FIG. 2. For purposes of non-limiting illustration and with reference to FIG. 2, a first treated aqueous stream is formed in first feeder unit 11 and forwarded through conduit 17 as described previously herein. A feed sanitizing aqueous stream is formed in second feeder unit 44 and forwarded through conduit 35 as described previously herein. Conduit 17 is in fluid communication with conduit 35 at intersection point 65. At intersection point 65 the first treated aqueous stream forwarded through conduit 17 is combined with the feed sanitizing aqueous stream forwarded through conduit 35, which results in the formation of a treated sanitizing aqueous stream that is forwarded from intersection point 65 through conduit 68. The treated sanitizing aqueous stream can be forwarded through conduit 68, with some embodiments, to a heat exchanger (not shown) where the temperature thereof is elevated so as to result in formation of the heated treated sanitizing aqueous stream. Alternatively, the treated sanitizing aqueous stream forwarded through conduit 68 can be combined with a heated third feed aqueous stream (not shown) for purposes of elevating the temperature thereof and resulting in the formation of the heated treated sanitizing aqueous stream.

The pH of the treated sanitizing aqueous stream forwarded through conduit 68 is measured by probe 56 in accordance with the description provided previously herein with regard to measurement of the pH of the treated sanitizing aqueous stream within mixing tank 32 of water treatment system 3 of FIG. 1.

In accordance with some embodiments of the present invention, formation of the treated sanitizing aqueous stream includes: providing a primary aqueous stream; forming a first treated aqueous stream, as described previously herein; combining the first treated aqueous stream with the primary aqueous stream; and combining a feed sanitizing aqueous stream with the primary aqueous stream, upstream and/or downstream of where the first treated aqueous stream is combined with the primary aqueous stream, thereby forming the treated sanitizing aqueous stream. With some further embodiments, the first treated aqueous stream is combined with the primary aqueous stream upstream and/or downstream of where the feed sanitizing aqueous stream is combined with the primary aqueous stream. The temperature of the treated sanitizing aqueous stream can be elevated by forwarding it to a heat exchanger so as to result in formation of the heated treated sanitizing aqueous stream. The feed sanitizing aqueous stream can be formed, with some embodiments, in accordance with the description provided previously herein.

With some embodiments, formation of the treated sanitizing aqueous stream includes: providing a primary aqueous stream; forming a first treated aqueous stream, as described previously herein; combining the first treated aqueous stream with the primary aqueous stream, thereby forming an intermediate primary aqueous stream; and combining a feed sanitizing aqueous stream with the intermediate primary aqueous stream, downstream of where the first treated aqueous stream is combined with the primary aqueous stream, thereby forming the treated sanitizing aqueous stream.

With some further embodiments, formation of the treated sanitizing aqueous stream includes: providing a primary aqueous stream; combining a feed sanitizing aqueous stream with the primary aqueous stream, thereby forming an intermediate primary aqueous stream; forming a first treated aqueous stream, as described previously herein; and combining the first treated aqueous stream with the intermediate primary aqueous stream, downstream of where the feed sanitizing aqueous stream is combined with the primary aqueous stream, thereby forming the treated sanitizing aqueous stream.

The primary aqueous stream can, with some embodiments, be selected from those sources as described previously herein with regard to the first and second feed aqueous streams, such as (but not limited to) city water.

Figure 3:
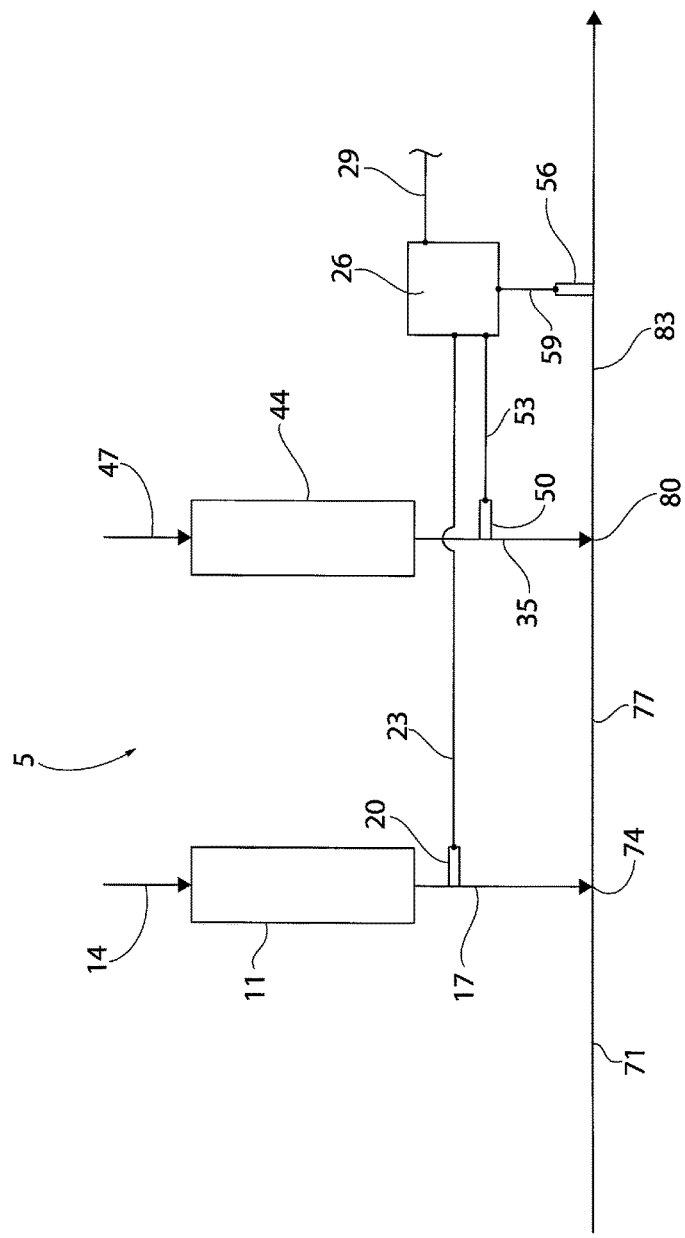
FIG. 3 is a schematic representation of a further water treatment system that can be used with a method according to the present invention.

For purposes of non-limiting illustration and with reference to the water treatment system 5 of FIG. 3, a primary aqueous stream is provided from a source (not shown) and forwarded through conduit 71 (or conduit segment 71). A treated aqueous stream is formed in feeder unit 11, as described previously herein, and combined with the primary aqueous stream at intersection point or junction 74 with conduit 71. The primary aqueous stream with the treated aqueous stream combined therewith (which can be referred to as an intermediate primary aqueous stream with some embodiments) is forwarded through conduit 77 (or conduit segment 77).

With further reference to FIG. 3, a feed sanitizing aqueous stream is formed in feeder unit 44 and forwarded through conduit 35 as described previously herein. The feed sanitizing aqueous stream is combined with the intermediate primary aqueous stream at intersection point or junction 80 with conduit (or conduit portion) 77, which results in the formation of a treated sanitizing aqueous stream that is forwarded through conduit (or conduit portion) 83. Intersection point 80 is downstream of intersection point 74, and intersection point 74 is upstream of intersection point 80. The treated sanitizing aqueous stream so formed can be forwarded to a heat exchanger (not shown) where the temperature thereof is elevated, thus resulting in the formation of the heated treated sanitizing aqueous stream. Alternatively, the treated sanitizing aqueous stream forwarded through conduit 83 can be combined with a heated third feed aqueous stream (not shown) for purposes of elevating the temperature thereof and resulting in the formation of the heated treated sanitizing aqueous stream.

The pH of the first aqueous feed stream forwarded through conduit 17, and the pH and/or conductivity of the feed sanitizing aqueous stream forwarded through conduit 35 can be measured by probes 20 and 50 and transmitted to process controller 26 by electrical connections 23 and 53 as described previously herein with regard to water treatment systems 3 and 4. The pH and/or conductivity of the treated sanitizing aqueous stream forwarded through conduit 83 can be measured with one or more probes, such as represented by probe 56, that are in probing contact with conduit 83, which can relay measurement data to processor controller 26 by electrical connection 59, as described previously herein. The amount and rate of, the primary aqueous stream flowing through conduit 71, the treated aqueous stream flowing through conduit 17, the feed sanitizing aqueous stream flowing through conduit 35, and the treated sanitizing aqueous stream flowing through conduit 83 can each be independently controlled by processor unit 26 by one or more valves (not shown).

With some further alternative embodiments, conduit 35 is in fluid communication with intersection point 74, and conduit 17 is in fluid communication with intersection point 80 (not depicted in FIG. 3), in which case the feed sanitizing aqueous stream is combined with the primary aqueous stream at intersection point 74, which results in the formation of an intermediate primary aqueous stream, which is forwarded through conduit 77. Correspondingly, downstream of where the feed sanitizing aqueous stream is combined with the primary aqueous stream (at intersection point 74), the first treated aqueous stream is combined with the intermediate primary aqueous stream at intersection point 80, which results in formation of the treated sanitizing aqueous stream, which is forwarded through conduit 83. The treated sanitizing aqueous stream can then be forwarded, with some embodiments, to a heat exchanger where the temperature thereof is elevated so as to result in the formation of the heated treated sanitizing aqueous stream.

The present invention is more particularly described in the examples that follow, which are intended to be illustrative only, since numerous modifications and variations therein will be apparent to those skilled in the art.

EXAMPLES

Two substantially equivalent commercial poultry immersion scalder lines were used in the present examples. One poultry immersion scalder line was operated with scalder make-up water that had been treated, in accordance with the present invention, and is referred to herein as a treated scalder line (or treated line, or treated scalder). The other poultry immersion scalder line was operated with scalder make-up water that had not been treated, and is referred to herein as an untreated scalder line (or untreated line, or untreated scalder). Each poultry immersion scalder had a total volume of 2700 gallons (10,221 liters) and a serpentine configuration with two bends (or turns), three parallel sections, and a total effective linear length of 90 feet (27.4 meters). Each scalder line was operated under counter-flow conditions, with chicken carcasses carried there-through in a first direction with their legs attached to shanks extending downward from an overhead conveyor, and water moving there-through in a second direction that was counter to the first direction. While moving through each scalder, the chicken carcasses were fully immersed.

The chicken carcasses used in the present examples were large broilers, typically having, a weight of 4.6 to 5.2 pounds (2.1 to 2.4 kilograms). The chicken carcasses were fully feathered and had not been eviscerated.

Each poultry immersion scalder line was operated at a chicken carcass throughput rate of 72 chicken carcasses per minute for about 16 hours per day. The water in each poultry immersion scalder line was maintained at a temperature of 131° F. to 133° F. (55° C. to 56° C.). Scalder make-up water (whether treated or untreated) was introduced into each scalder at three separate introduction (or drop) points, in each case at a rate of 10 gallons per minute (37.9 liters per minute) for a total of 30 gallons per minute (113.6 liters per minute) at a temperature of 131° F. to 133° F. (55° C. to 56° C.). Each scalder was operated so as to have an overflow rate (or scalder overflow rate) of 30 gallons per minute (113.6 liters per minute). The scalder overflow was forwarded to a water treatment system prior to being put to sewer or recycled.

The water used to initially fill each scalder was potable water. The untreated scalder make-up water was potable water. Potable water was used to prepare the treated scalder make-up water, as described further herein.

Treated scalder make-up water was prepared using a water treatment system similar to that depicted in FIG. 1 of the drawings and as described previously herein. Potable water was passed through a first feeder unit that contained ACID-RITE sodium bisulfate tablets (commercially available from Axiall, a Westlake Chemical company), which resulted in the formation of a first treated aqueous stream. Potable water was passed through a second feeder unit that contained ACCU-TAB calcium hypochlorite tablets (commercially available from Axiall, a Westlake Chemical company), which resulted in the formation of a second treated aqueous stream. The first treated aqueous stream and the second treated aqueous stream were combined in a mixing tank with a third heated aqueous stream (that was composed of heated potable water) so as to form a treated aqueous sanitizing stream, which was used as the treated scalder make-up water having a temperature of 131° F. to 133° F. (55° C. to 56° C.). The treated scalder make-up water had a free available chlorine content of about 300 ppm and a pH of 6.0 to 7.5. The free available chlorine content and pH of the treated scalder make-up water were each selected and adjusted appropriately so as to provide the overflow from the treated scalder (or treated scalder overflow) with a free available chlorine content of 0.05 ppm. The treated scalder make-up water was forwarded from the mixing tank through a conduit to a header where it was split into three separate conduits that were in fluid communication with the three separate introduction (or drop) points of the treated scalder.

Testing of the treated and untreated scalder lines was conducted over five separate days, with samples being obtained and evaluated as follows.

Chicken Carcass Testing:

On each of the five test days, 12 chicken carcasses were obtained in each case prior to entry into each of the treated and untreated scalder lines (pre-scald), and 12 chicken carcasses were obtained in each case after exiting each of the treated and untreated scalder lines (post-scald). Chicken carcasses were collected after at least one hour of continuous scalder line operation. In each case, the chicken carcasses were obtained in three rounds of four chicken carcasses per round, over a period of 30 to 45 seconds per round. Collection of all of the chicken carcasses typically took 60 to 90 minutes.

Each collected chicken carcass was evaluated using the Whole Carcass Rinse Method, which involved: allowing each collected chicken carcass to drain for 5 minutes; placing each drained chicken carcass in a plastic bag; adding 400 ml of an aqueous 1% buffered peptone solution to the plastic bag, and sealing it; gently shaking the sealed plastic bag about 20 times; pouring the liquid within the plastic bag into a suitable container, which was sealed and labeled; and then testing the collected liquid samples for the level of enterobacteriaceae present (in units of cfu/gram). The collected liquid samples were tested for enterobacteriaceae in accordance with accepted and reproducible industry standards.

The enterobacteriaceae test results obtained from the chicken carcasses collected over the five days of testing relative to the untreated scalder line are summarized in the following Table 1.

TABLE 1

| Untreated Scalder Line Chicken Carcass Results | | |
|---|---|---|
| | Total Enterobacteriaceae[3] (cfu/g) | Average Enterobacteriaceae[4] (cfu/g) |
| Pre-scald[1] | 155,254,700 | 2,587,578 |
| Post-scald[2] | 9,463,260 | 157,721 |
| Log Reduction[5] | 1.22 | 1.22 |

[1]Chicken carcasses that were collected prior to entry into the untreated scalder, and tested in accordnce with the Whole Carcass Rinse Method, as described above. The units of cfu/g means colony-forming unit per gram.
[2]Chicken carasses that were collected after exiting the untreated scalder, and tested in accordance with the Whole Carcass Rinse Method, as described above.
[3]The total enterobacteriaceae values were calculated from the sum of the enterobacteriaceae values obtained from each of the 60 chicken carcasses tested (12 chicken carcasses per day, for 5 days of testing).
[4]The average enterobacteriaceae values were obtained by dividing the total enterobacteriaceae values by 60.
[5]Log reduction was determined from the pre-scald and post-scald enterobacteriaceae values, using a viral load reduction calculator, such as available on the internet at the following link: www.jamesrbass.com/logReduction.htm.

The enterobacteriaceae test results obtained from the chicken carcasses collected over the five days of testing relative to the treated scalder line are summarized in the following Table 2.

TABLE 2

| Treated Scalder Line Chicken Carcass Results | | |
|---|---|---|
| | Total Enterobacteriaceae[3] (cfu/g) | Average Enterobacteriaceae[4] (cfu/g) |
| Pre-scald[6] | 43,020,000 | 717,000 |
| Post-scald[7] | 1,048,160 | 17,469 |
| Log Reduction[5] | 1.61 | 1.61 |

[6]Chicken carcasses that were collected prior to entry into the treated scalder, and tested in accordance with the Whole Carcass Rinse Method, as described above.
[7]Chicken carcasses that were collected after exiting the treated scalder, and tested in accordance with the Whole Carcass Rinse Method, as described above.

A comparison of the results summarized in Tables 1 and 2 above, demonstrates that chicken carcasses that were passed through a treated scalder line in accordance with the present invention had a significantly greater log reduction in enterobacteriaceae (1.61), as compared to chicken carcasses that were passed through an untreated scalder line (1.22). A further comparison of the log reduction results summarized in Tables 1 and 2 above, demonstrates that chicken carcasses that were passed through a treated scalder line in accordance with the present invention had a 32% further (or greater) reduction in enterobacteriaceae, as compared to chicken carcasses that were passed through an untreated scalder line: ((1.61−1.22)/1.22)×100.

Scalder Water Testing:

A single sample of water was obtained on each of the five test days from each of the treated scalder and the untreated scalder for a total of 10 samples (5 from the treated scalder, and 5 from the untreated scalder). The water samples were obtained, after at least three hours of continuous operation, from the scalder overflow. The scalder water samples were tested for enterobacteriaceae in accordance with accepted and reproducible industry standards.

The enterobacteriaceae test results obtained from the untreated and treated scalder water samples are summarized in the following Table 3.

TABLE 3

Untreated and Treated Scalders Water Sample Results

| | Total Enterobacteriaceae[8] (cfu/g) | Average Enterobacteriaceae[9] (cfu/g) |
|---|---|---|
| Untreated Scalder | 319,000 | 63,800 |
| Treated Scalder | 2817 | 563.4 |
| Log Reduction[10] | 2.05 | 2.05 |

[8] The sum of enterobacteriaceae values obtained from each of the 5 scalder water samples.
[9] The average enterobacteriaceae values were obtained by dividing the total enterobacteriaceae values by 5.
[10] Log reduction was determined from the untreated and treated scalder water sample enterobacteriaceae values, using a viral load reduction calculator, such as available on the internet at the following link: www.jamesrbass.com/logReduction.htm.

The results summarized in Table 3 demonstrate that a scalder treated in accordance with the present invention provides a significant reduction in enterobacteriaceae values as compared to an untreated scalder. In addition, the untreated scalder water samples were visually observed to be dark in color and opaque (they could not be seen through), and had a strong unpleasant odor; while the treated scalder water samples were visually observed to be pale yellow in color and clear (they could be seen through), and had no discernable odor. The visual observations were made on untreated and treated scalder water samples that were in equivalently dimensioned clear sample containers.

The present invention has been described with reference to specific details of particular embodiments thereof. It is not intended that such details be regarded as limitations upon the scope of the invention except insofar as and to the extent that they are included in the accompanying claims.

What is claimed is:

1. A method of sanitizing a surface comprising:
   (a) providing a pH control composition comprising at least one pH control agent comprising at least one bisulfate salt;
   (b) contacting a first feed aqueous stream with said pH control composition, thereby forming a first treated aqueous stream;
   (c) combining at least a portion of said first treated aqueous stream with a feed sanitizing aqueous stream comprising free available halogen from a source selected from the group consisting of calcium hypochlorite, sodium hypochlorite, potassium hypochlorite, lithium hypochlorite and combinations thereof, thereby forming a treated sanitizing aqueous stream comprising free available halogen;
   (d) elevating the temperature of the treated sanitizing aqueous stream, thereby forming a heated treated sanitizing aqueous stream having an elevated temperature that comprises free available halogen, wherein said heated treated sanitizing aqueous stream has a pH of about 6 to about 8;
   (e) applying said heated treated sanitizing aqueous stream to a surface to be sanitized.

2. The method of claim 1 wherein said elevated temperature of said heated treated sanitizing aqueous stream is at least 37° C. and less than 100° C.

3. The method of claim 2 wherein said elevated temperature of said heated treated sanitizing aqueous stream is at least 37° C. and less than or equal to 66° C.

4. The method of claim 1 wherein said heated treated sanitizing aqueous stream is applied to said surface to be sanitized by an application method selected from the group consisting of, wiping, immersion, curtain application, spray application, and combinations thereof.

5. The method of claim 1 wherein said surface to be sanitized is selected from the group consisting of vegetable surfaces, fruit surfaces, equipment surfaces, animal carcass surfaces, and combinations thereof.

6. The method of claim 1 wherein said surface to be sanitized is selected from the group consisting of poultry carcass surfaces, poultry processing equipment surfaces, and combinations thereof.

7. The method of claim 6 wherein said poultry processing equipment surfaces comprise at least one of poultry picker rails and poultry picking fingers.

8. The method of claim 6 wherein said heated treated sanitizing aqueous stream is applied to poultry carcass surfaces by at least partial immersion in a poultry scalder.

9. The method of claim 1 wherein said pH control agent further comprises at least one of an inorganic acid, an inorganic acid salt, an organic acid, and an organic acid salt.

10. The method of claim 1 wherein said pH control agent further comprises at least one of a carbonate salt, a bicarbonate salt, a carboxylic acid, a carboxylic acid salt, carbonic acid, and a hydrogen halide.

11. The method of claim 1, wherein said pH control agent comprises at least one bisulfate salt selected from alkali metal bisulfate, alkaline earth metal bisulfate, and combinations thereof.

12. The method of claim 11 wherein said pH control agent comprises an alkali metal bisulfate, an alkaline earth metal salt of a fatty carboxylic acid, and optionally a colorant.

13. The method of claim 12 wherein said alkali metal bisulfate comprises sodium bisulfate.

14. The method of claim 1 wherein said pH control composition is in the form of a tablet.

15. The method of claim 1 wherein said heated treated sanitizing aqueous stream comprises free available chlorine.

16. The method of claim 1 wherein said feed sanitizing stream is formed by contacting a second feed aqueous stream with a source of free available halogen.

17. The method of claim 16 wherein said source of free available halogen further comprises chlorine gas, 1,3,5-trichloro-1,3,5-triazine-2,4,6-trione, 1-bromo-3-chloro-5,5-dimethylhydantoin or combinations thereof.

18. The method of claim 1 wherein said elevated temperature of said heated treated sanitizing aqueous stream is at least 37° C. (98° F.) and less than or equal to 54° C. (130° F.).

* * * * *